United States Patent
Kim et al.

(10) Patent No.: US 10,434,128 B2
(45) Date of Patent: Oct. 8, 2019

(54) COMPOSITION COMPRISING ULMI CORTEX EXTRACTS FOR INHIBITING OVOTOXICITY

(71) Applicant: DONGGUK UNIVERSITY GYEONGJU CAMPUS INDUSTRY-ACADEMY COOPERATION FOUNDATION, Gyeongju-si, Gyeongsangbuk-do (KR)

(72) Inventors: Dong Il Kim, Goyang-si (KR); Ju Hee Lee, Goyang-si (KR); Deok Ho Kim, Seoul (KR); Jae Hyun Han, Seoul (KR); Su Hyun Kim, Goyang-si (KR)

(73) Assignee: Dongguk University Gyeongju Campus Industry-Academy Cooperation Foundation (KR)

( * ) Notice: Subject to any disclaimer, the term of this patent is extended or adjusted under 35 U.S.C. 154(b) by 0 days.

(21) Appl. No.: 16/021,952

(22) Filed: Jun. 28, 2018

(65) Prior Publication Data

US 2019/0000901 A1 Jan. 3, 2019

(30) Foreign Application Priority Data

Jul. 3, 2017 (KR) ........................ 10-2017-0084034

(51) Int. Cl.
*A61K 36/185* (2006.01)
*A61P 15/00* (2006.01)

(52) U.S. Cl.
CPC ............ *A61K 36/185* (2013.01); *A61P 15/00* (2018.01); *A61K 2236/331* (2013.01)

(58) Field of Classification Search
CPC .. A61K 2300/00; A61K 36/185; A61K 36/71; A61K 36/258; A61K 36/484; A61K 36/716; A61K 36/9068; A61K 35/32; A61K 36/284; A61K 36/42; A61K 36/481; A61K 36/534; A61K 36/538; A61K 36/725; A61K 36/734; A61K 36/752; A61K 36/8998; A61K 36/9064; A61K 2236/00; A61K 36/00; A61K 36/28; A61K 36/23; A61K 36/282; A61K 36/31; A61K 36/54; A61K 36/61; A61K 36/739; A61K 36/87; A23L 33/105; A23L 17/50; A23V 2002/00; A23V 2200/32; A23V 2200/30; A23V 2200/308; A23V 2200/332; Y10S 514/909
See application file for complete search history.

(56) References Cited

U.S. PATENT DOCUMENTS

2011/0052731 A1* 3/2011 Park ..................... A61K 36/185
424/728

FOREIGN PATENT DOCUMENTS

| KR | 100937394 B | 1/2010 |
| KR | 1020160115381 A | 10/2016 |
| KR | 1020160134925 A | 11/2016 |

OTHER PUBLICATIONS

Kim, "Determination of the protective efficacy of Ulmi cortex Water extract against ovotoxicity and a proposal for its clinical use" (21 pages) (English Abstract only), (2016).
Yang et al. "Asian Elm tree inner bark prevents articular cartilage deterioration in ovariectomized obese rats with monoiodoacetate-induced osteoarthritis" Menopause 23(2): 197-208 (2016).

* cited by examiner

*Primary Examiner* — Aaron J Kosar
(74) *Attorney, Agent, or Firm* — Myers Bigel, P.A.

(57) ABSTRACT

Provided is a method of treating ovotoxicity of an individual, including administering an *Ulmi* cortex extract to an individual in need of treatment. The present disclosure may exhibit an effect of preventing, alleviating, or treating ovarian aging or premature ovarian failure by inhibiting oxidative stress or ovotoxicity of the ovaries.

3 Claims, 9 Drawing Sheets

COMPOSITION COMPRISING ULMI CORTEX EXTRACTS FOR INHIBITING OVOTOXICITY

CROSS-REFERENCE TO RELATED APPLICATION

This application claims the benefit of Korean Patent Application No. 10-2017-0084034, filed on Jul. 3, 2017, in the Korean Intellectual Property Office, the disclosure of which is incorporated herein in its entirety by reference.

BACKGROUND

1. Field

The present disclosure relates to a method of inhibiting ovotoxicity, including administering an *Ulmi* cortex extract (UCE).

2. Description of the Related Art

Women's aging can be classified as general body aging that occurs generally throughout the body and the aging of a reproductive function. As the Discourse on Heavenly Genuineness in Remote Antiquity in <The Yellow Emperor's Inner Classic (Huangdi Neijing)> mentions that women's aging proceeds according to the utmost exhaustion of the heavens, which means menopause, the aging of reproductive functions is of importance, which may also be referred to as ovarian aging.

Although ovarian aging is a common phenomenon in all women, ovarian aging may occur early or be relatively delayed due to individual differences, but at the age of 35, the number of follicles is reduced and the quality of oocytes is lowered, which leads to reduced fertility.

Ovotoxicity refers to toxic effects of various harmful factors on ovarian tissues and germ cells of the ovary. Anti-cancer chemotherapeutic agents, polycyclic aromatic hydrocarbons (PAHs), and the like are known as representative ovotoxic factors. Such ovotoxicity triggers ovarian aging, thus causing premature ovarian failure or impaired fertility.

In oriental medicine, a therapeutic method of rejuvenating the body is basically adopted for preventing and treating subfertility or in clinical trials of premature ovarian failure which leads to menopause due to an early decline in ovarian function, and this may be regarded due to the fact that the origin of ovarian aging is attributed to impotence. However, despite this point of view, it is difficult to adequately treat subfertility due to ovarian aging according to age increase only by using this therapeutic method, and more suitable clinical methods for the prevention and treatment of premature ovarian failure are insufficient.

SUMMARY

Therefore, the inventors of the present disclosure conducted research on natural substances having an ovotoxicity inhibitory effect, i.e., an effect of protecting cells from ovotoxicity, and discovered that the *Ulmi* cortex, which is obtained by drying the bark of a tree obtained by peeling the cork layer of the *Ulmus macrocarpa* Hance, had a protective effect against ovotoxicity, thus completing the present disclosure.

Throughout the present specification, many papers and patent documents are referred to and citations thereof are shown. The disclosures of the cited papers and patent documents are incorporated herein by reference in their entirety, and thus the level of the art to which the present disclosure pertains and the contents of the present disclosure will be explained more clearly.

Provided are methods of inhibiting ovotoxicity of an individual, including administering an *Ulmi* cortex extract to an individual in need thereof.

Provided are methods of treating ovarian aging or premature ovarian failure, including administering an *Ulmi* cortex extract to an individual in need of treatment.

Additional aspects will be set forth in part in the description which follows and, in part, will be apparent from the description, or may be learned by practice of the presented embodiments.

According to an aspect of an embodiment, a method of inhibiting ovotoxicity of an individual includes administering an *Ulmi* cortex extract to an individual in need of treatment.

According to one embodiment, the *Ulmi* cortex extract may prevent or treat ovarian aging caused by ovotoxicity.

According to one embodiment, the ovarian aging may be premature ovarian failure or early menopause.

According to one embodiment, the *Ulmi* cortex extract may be administered in the form of a pharmaceutical composition, and the *Ulmi* cortex extract may be included in the composition at a concentration of about 100 µg/ml to about 300 µg/ml.

According to one embodiment, the *Ulmi* cortex extract may be a water extract.

According to one embodiment, the *Ulmi* cortex extract may be a hot-water extract.

According to an aspect of another embodiment, there is provided a food composition for preventing or alleviating ovarian aging, which includes the *Ulmi* cortex extract.

According to an aspect of another embodiment, a method of treating ovarian aging or premature ovarian failure includes administering the *Ulmi* cortex extract to an individual in need of treatment.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
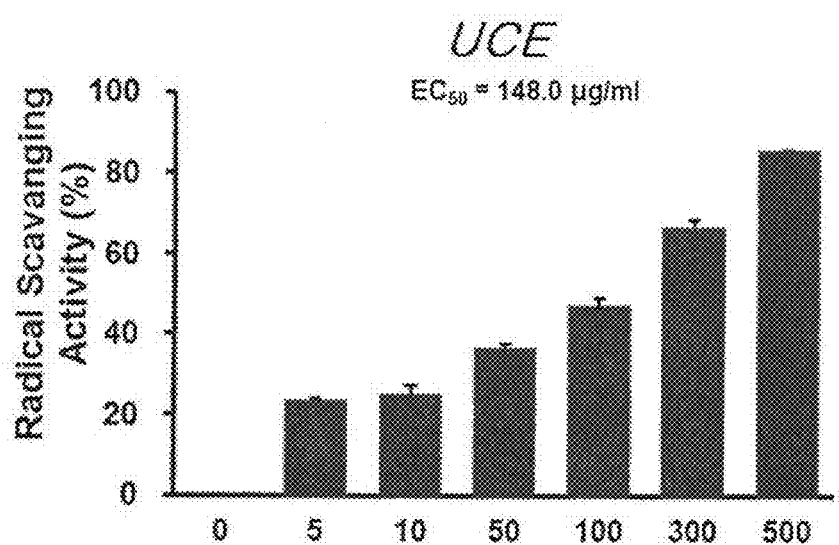
FIG. 1 illustrates the DPPH-radical scavenging activity and $EC_{50}$ of an *Ulmi* cortex extract according to the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

One embodiment of the present disclosure provides a method of inhibiting ovotoxicity of an individual, including administering an *Ulmi* cortex extract to an individual in need of treatment.

According to one embodiment, the *Ulmi* cortex extract may prevent or treat ovarian aging caused by ovotoxicity.

According to one embodiment, the ovarian aging may be premature ovarian failure or early menopause.

As used herein, the term "ovotoxicity" refers to a toxic effect on ovarian tissues and ovarian germ cells, which is exhibited by various harmful factors, and ovotoxicity is known to induce premature ovarian failure or impaired fertility by triggering ovarian aging (Advances in Experimental Medicine and Biology. 2001; 500:73-81).

The expression "inhibition of ovotoxicity" as used herein refers to inhibition of an effect such as apoptosis due to ovotoxicity, and is interchangeably used with ovotoxicity protection or protection from ovotoxicity.

The term "ovarian aging" as used herein refers to a reduction in reproductive ability due to aging of ovarian tissues and ovarian germ cells, and ovarian aging may cause premature ovarian failure or infertility.

The term "premature ovarian failure" as used herein refers to temporary cessation of an ovarian function before the age of 40, and is defined as a hypergonadotropic state at amenorrheal and menopausal levels. The premature ovarian failure occurs due to various causes such as genetic abnormalities, ovariectomy, autoimmune diseases, chromosomal abnormalities, radiotherapy, anticancer treatment, smoking, and the like, but it has been reported that in most cases, since the cause of the premature ovarian failure is unclear, treatment thereof is also not easy (Syst Biol Reprod Med. 2012; 58(1):57-62).

The term "premature menopause" as used herein refers to menopause occurring before the age of 40, and it is known that premature menopause occurs in 1% of all women and is a disease that commonly occurs in one in 1,000 women even before the age of 30.

The term "*Ulmi* cortex" as used herein refers to a dried product of the bark obtained by peeling the cork layer of *Ulmus macrocarpa* Hance, and is also referred to as *Ulmi pumilae* cortex, cortex ulmi pumilae, or the like.

The *Ulmi* cortex extract (UCE) according to the present disclosure includes all substances obtained by extracting components of the *Ulmi* cortex, regardless of an extraction method, an extraction solvent, extracted components, or extract form. The *Ulmi* cortex extract includes a substance obtained using an extraction method including a process of treating with heat, an acid, a base, an enzyme, or the like in a process of extracting components of the *Ulmi* cortex extract and also includes a substance obtained by performing additional processing or treatment, e.g., fermentation or enzymatic treatment, on an extract of an *Ulmi* cortex component.

The subject of extraction of the *Ulmi* cortex component includes other processed *Ulmi* cortex materials, such as crude *Ulmi* cortex, a dried, fermented, or dried pulverized product thereof, and the like. The extraction of the *Ulmi* cortex component of the present disclosure may be performed using any one method selected from the group consisting of reflux extraction, hot water extraction, high pressure extraction, and microwave extraction, but the present disclosure is not limited to the above examples.

According to one embodiment, the *Ulmi* cortex extract is obtained by drying the *Ulmi* cortex and then performing reflux extraction thereon using water including distilled water, an organic solvent, or a combination thereof, and this method may further include removing a liposoluble component from the *Ulmi* cortex extract and extracting and concentrating the resulting *Ulmi* cortex extract. The organic solvent may be a solvent selected from the group consisting of an alcohol with 1 to 20 carbon atoms, acetone, ethyl acetate, diethyl ether, ethyl methyl ketone, and chloroform, but the present disclosure is not limited to the above examples.

According to one embodiment, the *Ulmi* cortex extract may be a water extract.

According to one embodiment, the *Ulmi* cortex extract may be a hot-water extract.

According to one embodiment, the *Ulmi* cortex extract may be an extract obtained by a solvent selected from the group consisting of methanol, ethanol, propanol, butanol, pentanol, and a combination thereof.

Extraction method and condition may be appropriately selected by one of ordinary skill in the art.

In one embodiment, the *Ulmi* cortex extract may inhibit the apoptosis of ovarian cells.

In one embodiment, the *Ulmi* cortex extract may activate the PI3K/Akt signaling pathway.

In one embodiment, the *Ulmi* cortex extract may be administered in the form of a pharmaceutical composition, and the *Ulmi* cortex extract may be included in the composition at a concentration of about 100 μg/ml to about 300 μg/ml.

An embodiment of the present disclosure provides a pharmaceutical composition for inhibiting ovotoxicity, which includes the above-described *Ulmi* cortex extract.

The pharmaceutical composition of the present disclosure may further include a pharmaceutically acceptable carrier, an excipient, or a diluent. The pharmaceutically acceptable carrier, the excipient, or the diluent, which may be used in the present disclosure, is not particularly limited as long as it does not adversely affect the effects of the present disclosure, and non-limiting examples thereof include a filler, an extender, a binder, a wetting agent, a disintegrating agent, a surfactant, a lubricant, a sweetener, a flavoring agent, and a preservative. Non-limiting representative examples of the pharmaceutically acceptable carrier, the excipient, or the diluent include lactose, dextrose, sucrose, sorbitol, mannitol, xylitol, maltitol, starch, gelatin, glycerin, acacia rubber, alginate, calcium phosphate, calcium carbonate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, propylene glycol, polyethylene glycol, a vegetable oil, an injectable ester, Witepsol, Macrogol, Tween 61, cacao butter, and laurin butter.

The pharmaceutical composition of the present disclosure may be in the form of one selected from the group consisting of tablets, pills, powder, granules, capsules, a suspension, an emulsion, a syrup, an aerosol, an agent for external application, a suppository, and an injection. The pharmaceutical composition may be formulated according to a method commonly known in the art, and the formulation method is not particularly limited.

The pharmaceutical composition of the present disclosure may be administered orally or parenterally, a suitable dose thereof may be appropriately selected according to age, gender and body weight of a subject to which the pharmaceutical composition is to be administered, conditions, the severity of diseases, drug form, administration route, and administration period, and the pharmaceutical composition may be generally administered in an amount of about 5 mg/kg to about 500 mg/kg, for example, about 100 mg/kg to about 250 mg/kg once to three times a day.

It is obvious to those of ordinary skill in the art that the formulation method, dosage, administration route, ingredients, and the like of the pharmaceutical composition of the present disclosure may be appropriately selected from the general techniques known in the art.

The pharmaceutical composition of the present disclosure may further include, in addition to the *Ulmi* cortex extract as an active ingredient, other pharmaceutically active ingredients, or may be used in combination with a pharmaceutical composition including other active ingredients.

An embodiment of the present disclosure provides a food composition for preventing or alleviating ovarian aging, which includes the above-described *Ulmi* cortex extract.

In one embodiment, the composition may include the *Ulmi* cortex extract at a concentration of about 100 µg/ml to about 300 µg/ml. The amount of the *Ulmi* cortex extract in the composition may be appropriately determined by one of ordinary skill in the art according to the purpose of use and need.

In one embodiment, the *Ulmi* cortex extract may be a water extract.

In one embodiment, the *Ulmi* cortex extract may be obtained through extraction using an extraction solvent commonly used in the art, such as water, an organic solvent, or the like.

The term "food" as used herein is intended to include meats, sausages, bread, chocolates, candies, snacks, confectionaries, pizzas, instant noodles, other noodles, gums, dairy products including ice creams, various kinds of soup, beverages, tea, drinks, alcoholic drinks, vitamin complexes, functional foods, and health foods, and all foods in the ordinary sense are included.

The term "functional food" refers to a food with high pharmaceutical and medical effects, which is processed to efficiently exhibit body modulating function as well as nutritional supply. The term "functionality" as used herein refers to controlling nutrients for the structure and functions of the human body or providing useful effects of hygienic purposes, such as psychological effects, and the like.

The food composition of the present disclosure may be prepared using a method commonly used in the art, and may be prepared by adding raw materials and ingredients that are commonly added in the art. In addition, the functional food may be prepared in any dosage form as long as the dosage form is a dosage form regarded as a functional food.

The composition may include an additional ingredient capable of enhancing smell, taste, vision, or the like commonly used in a food composition. For example, the additional ingredient may include vitamins A, C, D, E, B1, B2, B6, and B12, niacin, biotin, folate, panthotenic acid, and the like. In addition, the additional ingredient may include a mineral such as zinc (Zn), iron (Fe), calcium (Ca), chromium (Cr), magnesium (Mg), manganese (Mn), copper (Cu), or the like. In addition, the additional ingredient may include an amino acid such as lysine, tryptophan, cysteine, valine, or the like.

In addition, the composition may include food additives such as an antiseptic agent (potassium sorbate, sodium benzoate, salicylic acid, sodium dehydroacetate, or the like); a disinfectant (bleaching powder and high-grade bleaching powder, sodium hypochlorite, or the like); an antioxidant (butylhydroxyanisole (BHA), butylhydroxytoluene (BHT), or the like); a colorant (tar pigment or the like); a color fixing agent (sodium nitrite, or the like); a bleaching agent (sodium sulfite); a seasoning agent (sodium glutamate (MSG), or the like); a sweetener (dulcin, cyclamate, saccharin, sodium, or the like); a flavor (vanillin, lactones, or the like); an inflating agent (alum, potassium D-bitartrate, or the like), a fortifying, agent, an emulsifying agent, a thickener (thickening agent), a coating agent, a gum base agent, an anti-foaming agent, a solvent, a modifier, and the like. The additives may be selected according to the type of food and used in an appropriate amount.

Example 1. Preparation of *Ulmi* Cortex Extract

The used *Ulmi* cortex extract was carefully selected from medical herbs purchased from OMNIHERB. 100 g of the *Ulmi* cortex extract was added to 800 ml of distilled water, followed by heating reflux extraction at 90° C. for 4 hours. The resulting extract was cooled at room temperature and filtered twice with 8 µm filter paper, and the filtrate was concentrated under reduced pressure at 40° C. and lyophilized to be prepared into powder form, followed by quantification. The obtained *Ulmi* cortex extract had a yield of 10.9%(=10.9 g/100 g).

Example 2. Measurement of Antioxidant Activity of *Ulmi* Cortex Extract

Antioxidant activity is known to play a major role in preventing the aging of human organs and diseases caused thereby. Thus, since it can be expected that reproductive aging is inhibited by antioxidant activity, the antioxidant activity of the *Ulmi* cortex extract prepared according to Example 1 was measured.

2-1. Measurement of Scavenging Activity of DPPH Radical

The scavenging activity of the 1,1-diphenyl-2-picrylhydrazyl (DPPH) radical was measured using a method described in a document [Gyamfi M A et al., Free-radical scavenging action of medicinal herbs from Ghana Thonningia sanguinea on experimentally induced liver injuries. Gen Pharmacol. 1999; 32:661-7].

First, 1 ml of a 1M DPPH solution and 450 µl of a 50 µM Tris-HCl buffer (pH 7.4) were added to 50 µl of an *Ulmi* cortex extract sample, and then mixed. The resulting mixture was allowed to react at room temperature for 30 minutes, and then absorbance thereof was measured at 517 nm using a microplate reader (VersaMax, Molecular Devices, USA). The scavenging activity of the DPPH radical was expressed as a concentration with 50% scavenging activity ($EC_{50}$, effective concentration 50%).

As a result of examining a free radical scavenging function by the DPPH method, the $EC_{50}$ value of the *Ulmi* cortex extract was 148.0 μg/ml. FIG. 1 illustrates the radical scavenging activity of an *Ulmi* cortex extract according to concentration (μg/ml) increase.

2-2. Measurement of Scavenging Activity of Superoxide Anion

The scavenging activity of a superoxide anion, which is another indicator of antioxidant activity and one of the representative reactive oxygen species, was measured using a nitro blue tetrazolium (NBT) reduction method. The scavenging activity of the superoxide anion was measured using a method described in a document after being partially modified [Gotoh N, Niki E. Rates of interactions of superoxide with vitamin E, vitamin C and related compounds as measured by chemiluminescence. Biochim Biophys Acta. 1992; 1115:201-7].

In particular, 10 μl of 30 mM EDTA (pH 7.4), 1 μl of 30 mM hypoxanthine, and 200 μl of 1.42 mM NBT were added to 30 μl of an *Ulmi* cortex extract sample, and allowed to react at room temperature for 3 minutes. Subsequently, 10 μl of 1 U/ml xanthine oxidase was added to the resulting reaction product and the total volume was adjusted to 300 μl with 50 mM phosphate buffer (pH 7.4). The reaction solution was incubated at room temperature for 20 minutes, and then absorbance thereof was measured at a wavelength of 560 nm. For analysis, the results were converted to and expressed as $EC_{50}$ values, which indicates NBT reduction by a superoxide anion.

Figure 2:
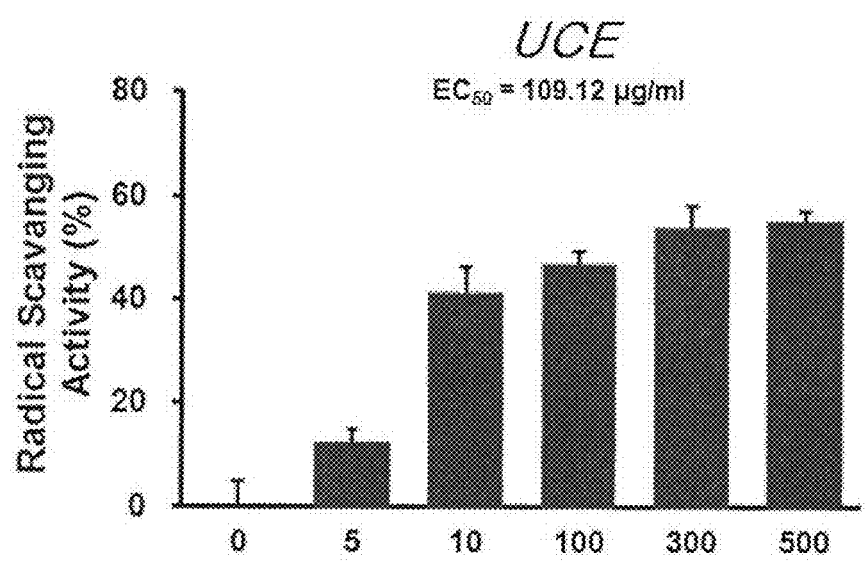
FIG. 2 illustrates the superoxide anion radical scavenging activity and $EC_{50}$ of an *Ulmi* cortex extract according to the present disclosure.

As a result of the experiment, the $EC_{50}$ value of the UCE was confirmed as 109.12 μg/ml. FIG. 2 illustrates the radical scavenging activity of an *Ulmi* cortex extract according to concentration increase.

Example 3. Measurement of Cell Viability (MTT Assay)

The cytotoxicity of the *Ulmi* cortex extract of Example 1 was measured using a 3-(4,5-dimethylthiaxzol-2-yl)-2,5-diphenyltetrazolium bromide (MTT) assay. The MTT assay is a method of measuring cell viability using cell capacity to reduce MTT tetrazolium, which is a yellow water-soluble substrate, to blue-violet non-aqueous MTT formazan through dehydrogenase action.

CHO-K1 cells (Chinese hamster ovary cells, $2\times10^4$ cells/well) were cultured in a 48-well plate and subjected to serum starvation for 4 hours, and then treated with 10 μg/ml, 50 μg/ml, 100 μg/ml, 300 μg/ml, or 500 μg/ml of the *Ulmi* cortex extract, followed by incubation at 37° C. under 5% $CO_2$ for 24 hours. 30 μl of an MTT solution (2 mg/ml) was added to each well and allowed to react in a 5% $CO_2$ incubator at 37° C. for 3 hours, and then the MTT solution and the culture solution were completely removed, and formazan crystals formed in the cells were dissolved with 150 μl of dimethyl sulfoxide (DMSO, Sigma-Aldrich, USA) and absorbance thereof was measured at 595 nm using an ELISA plate reader (DYNEX, Opsys MR, USA). For analysis, the results were expressed as the percentage of cell viability with respect to a control not treated with the *Ulmi* cortex extract. Absorbance according to concentration was corrected while comparing the absorbance of a control with the absorbance of the experimental group after culturing along with a medium except for the cells.

Figure 3:
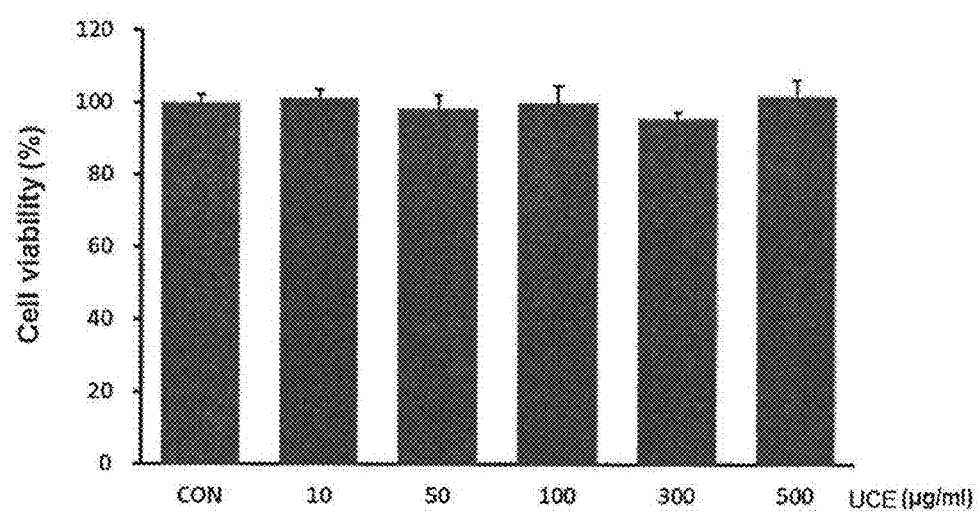
FIG. 3 illustrates a concentration-dependent effect of an *Ulmi* cortex extract according to the present disclosure on CHO-K1 cell viability.

As illustrated in FIG. 3, it was confirmed that the *Ulmi* cortex extract did not affect the viability of CHO-K1 cells up to a concentration of 500 μg/ml.

Example 4. Effect of UCE on Inhibiting Ovotoxicity 4-vinylcyclohexene diepoxide (VCD) is a representative ovotoxicity-inducing material, and a toxic effect of VCD is expressed through the apoptosis and necrosis of ovarian follicles. VCD is known to reduce the viability of oocytes by damaging primordial oocytes and follicles, and cause ovotoxicity, which corresponds to a menopausal level, by causing reproductive dysfunction (Syst Biol Reprod Med. 2012; 58(1):57-62).

CHO-K1 cells were pre-treated with the Ulmin cortex extract at various concentrations (5 μg/ml, 10 μg/ml, 50 μg/ml, 100 μg/ml, and 300 μg/ml) for 2 hours and treated with 1.5 mM VCD to cause ovotoxicity. Thereafter, the viability of the CHO-K1 cells was measured using an MTT assay to identify an effect of the Ulmin cortex extract on inhibiting ovotoxicity, i.e., a protective effect of the Ulmin cortex extract against ovotoxicity, according to concentration.

Figure 4:
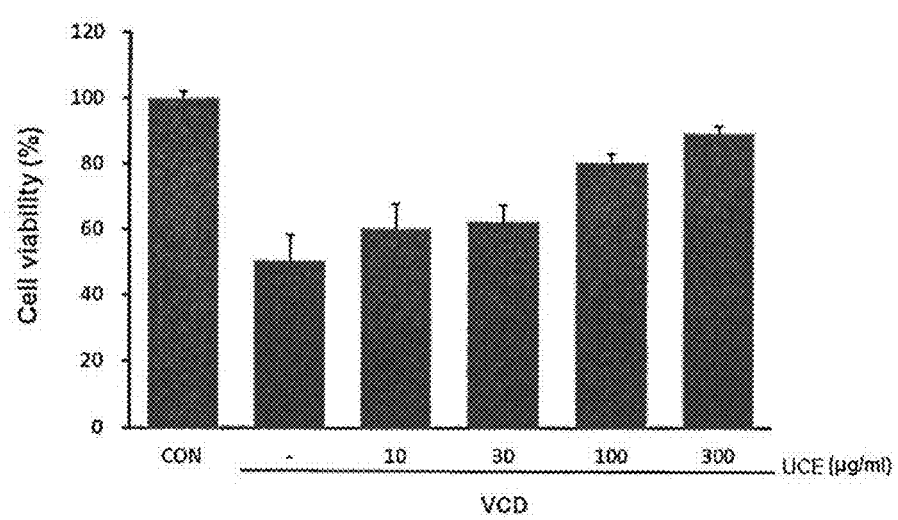
FIG. 4 illustrates a concentration-dependent effect of an *Ulmi* cortex extract according to the present disclosure on the viability of CHO-K1 cells with ovotoxicity induced by 4-vinylcyclohexene diepoxide (VCD)

As illustrated in FIG. 4, the *Ulmi* cortex exhibited an effect of protecting CHO-K1 cells from ovotoxicity in a concentration-dependent manner, and exhibited the highest viability at a concentration of 300 μg/ml. Based on these results, 300 μg/ml of the *Ulmi* cortex extract was used in subsequent experiments.

Example 5. Effect of *Ulmi* Cortex Extract on VCD-Inducing Apoptosis 5-1. Cell Morphology Observation Through cell morphological changes, it was confirmed whether the *Ulmi* cortex extract protected CHO-K1 cells from cell damage induced by VCD.

First, cells were distributed into a 96-well plate at a density of $1\times10^4$ cells/well, and the cells were cultured until the next day, followed by serum starvation for 4 hours. Subsequently, the cells were pre-treated with 300 μg/ml of the *Ulmi* cortex extract for 4 hours and treated with 1.5 mM VCD, and then incubated at 37° C. under 5% $CO_2$ for 24 hours, and the cells were observed using an optical microscope (Nikon, Japan).

Figure 5:
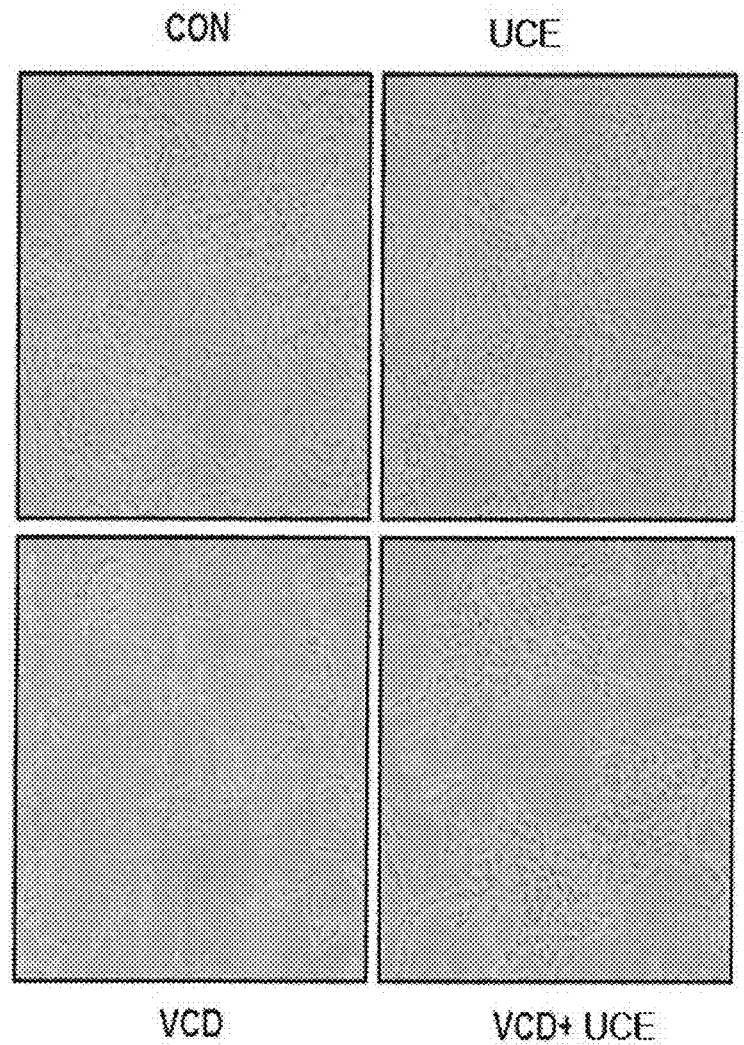
FIG. 5 illustrates cell morphological observation results showing an ovotoxicity protective effect of an *Ulmi* cortex extract according to the present disclosure on the viability of CHO-K1 cells with ovotoxicity induced by VCD (CON: control; UCE: treated with an *Ulmi* cortex extract; VCD: treated with VCD; VCD+UCE: pre-treated with an *Ulmi* cortex extract and then treated with VCD)

As illustrated in FIG. 5, apoptosis was observed in a group (VCD) treated only with VCD, and a group (UCE) treated only with the UCE exhibited the same cell morphology compared to a control (CON) treated with none, from which it was confirmed that the UCE had no toxicity to the cells. In contrast, in the case of a group (VCD+UCE) simultaneously treated with the UCE and VCD, cells grew similarly to a VCD-untreated group, from which it was confirmed that the *Ulmi* cortex extract had a protective effect against VCD-induced ovotoxicity.

5.2. Western Blot Analysis

As confirmed in Example 4, when CHO-K1 cells were treated with VCD, apoptosis occurred. To examine an effect of pretreatment with the *Ulmi* cortex extract (300 μg/ml), proteins associated with apoptosis, i.e., poly(ADP-ribosyl) polymerase (PARP) and caspase-3, were identified through western blot analysis.

As described in Example 5-1, a protein sample was collected from CHO-K1 cells pretreated with 300 µg/ml of the *Ulmi* cortex extract for 2 hours and treated with 1.5 mM VCD. For this, the cells treated with VCD were washed three times with PBS, RIPA buffer was added thereto, and the resulting cells were allowed to react at 4° C. for 30 minutes and then centrifuged at 12,000 rpm for 30 minutes to collect a supernatant, and proteins were extracted therefrom. Subsequently, the same amount of the proteins were separated on a sodium dodecyl sulfate-polyacrylamide gel electrophoresis (SDS-PAGE), and then transferred to a PVDF membrane. To block non-specific binding, the membrane was treated with a blocking buffer (5% skim milk) for 1 hour, and washed with a PBST solution containing 0.1% Tween 20. Thereafter, the membrane was allowed to react with primary antibodies against PARP and caspase-3 at 4° C. overnight. Subsequently, the membrane was treated with a HRP-conjugated anti-rabbit or anti-mouse antibody as a secondary antibody (Santa Cruz Biothechnology. Inc., Santa Cruz. Calif., USA), and developed using an ECL chemiluminescence detection reagent, and then western blotting results were identified using an image analyzing system.

Figure 6:
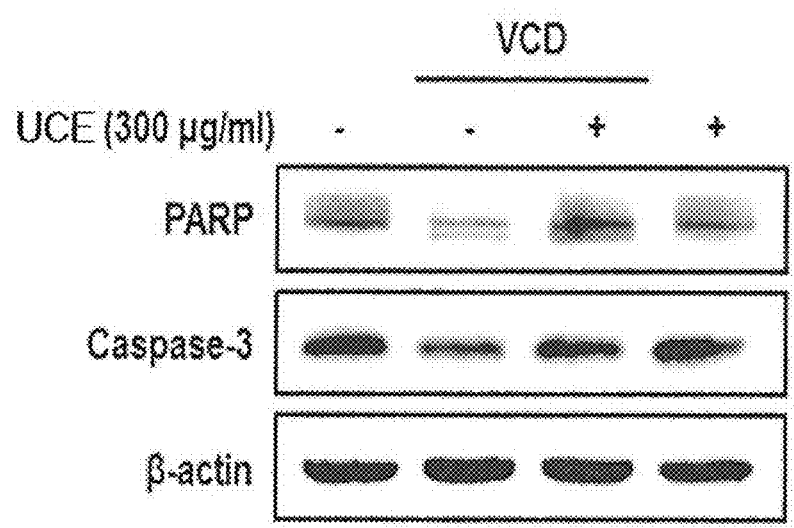
FIG. 6 illustrates PARP and caspase-3 western blot analysis results showing an ovotoxicity protective effect of an *Ulmi* cortex extract according to the present disclosure in CHO-K1 cells with VCD-induced ovotoxicity.

As illustrated in FIG. 6, in the case of the group treated only with VCD, the proform band of PARP decreased and the proform band of caspase-3 became pale compared to a control, from which it was confirmed that apoptosis progressed. In contrast, in the case of the group pretreated with the UCE and treated with VCD, the proform band of PARP did not decrease and the proform band of caspase-3 did not become pale compared to the group treated only with VCD. From these results, it was confirmed that the case of treatment with the UCE exhibited an effect of protecting cells from ovotoxicity due to VCD.

Example 6. Mechanism of Ovotoxicity Inhibition by *Ulmi* Cortex Extract

To examine a mechanism for a protective effect of the *Ulmi* cortex extract against ovotoxicity, an effect of the *Ulmi* cortex extract on the PI3K/Akt signaling, which is known as the toxic mechanism of VCD, was examined through western blot analysis.

An experiment was conducted in the same manner as in Example 5-2, except that in western blotting, phospho-AKT, total-Akt, mTOR, phospho-mTOR, GSK-3β, phospho-GSK-3β, β-actin, and phospho-FoxO3a (Cell Signaling Technology, Danvers, Mass., USA) were used as the primary antibodies against the proteins.

Figure 7:
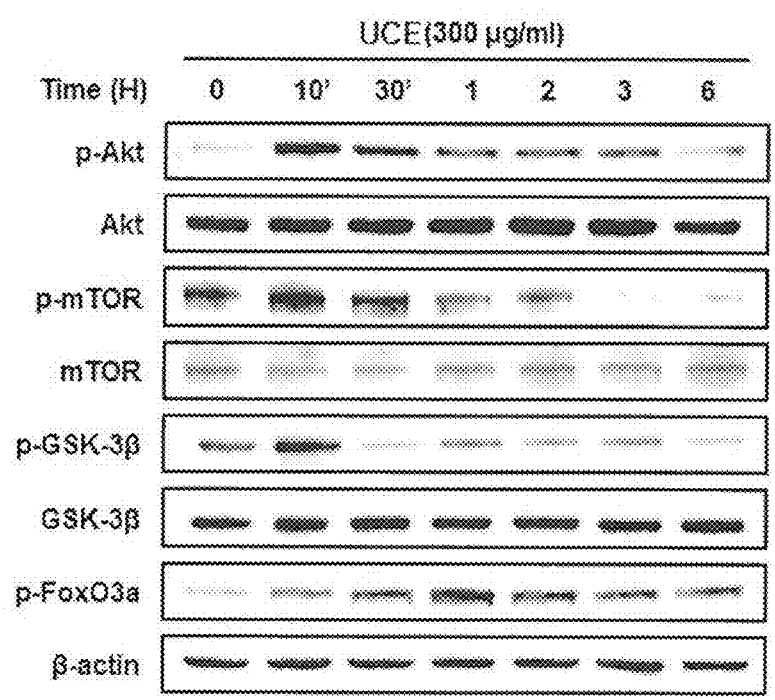
FIG. 7 illustrates western blot analysis results of key factors (Akt, mTOR, and GSK-3beta) of the PI3K/AKT signaling pathway, which showed an effect of an *Ulmi* cortex extract according to the present disclosure on the PI3K/AKT signaling pathway.

As illustrated in FIG. 7, as treatment time elapsed, activation proceeded towards a lower signal of the PI3K/Akt signaling pathway. As a result of identifying Akt, mTOR, and GSK-3, which correspond to three major signaling kinases of PI3K/Akt, by comparison with a control through western blot analysis, the *Ulmi* cortex extract was seen to activate the PI3K/Akt signaling pathway according to particular reaction time, and it was confirmed that the *Ulmi* cortex extract component changed into a normal signaling pathway while activating the PI3K family.

Example 7. Effect of UCE on Preventing Ovarian Failure In Vivo

An inhibitory effect of the *Ulmi* cortex extract on ovotoxicity and a protective effect thereof against ovarian failure according thereto were examined using an animal model.

7-1. Experimental Animal

B6C3F1 female mice at the age of 3 weeks (10 g to 12 g) from the same date of birth (DOB) as an experimental animal were purchased from the Central Lab Animal Inc., were adapted to a laboratory environment while sufficiently fed feed and water, and then used in an experiment. The laboratory environment was maintained at a temperature of 22±2° C. and a 12-hour day/12-hour night cycle was maintained until the experiment was completed. All experimental processes and procedures related to animal experiments used in this study were carried out in accordance with the preliminary examination and ethical regulations of the Animal Experiment Ethics Committee of Dongguk University.

7-2. Premature Ovarian Failure Induction

A control and a group treated only with *Ulmi* cortex (UCE 300 mg/kg) were intraperitoneally injected with sesame oil (Sigma-Aldrich, USA), and a negative control (VCD), a positive control (VCD+Mertformin 100 mg/kg, VCD+MET), and an experimental group ((VCD+UCE 300 mg/kg) were intraperitoneally injected with VCD (Sigma-Aldrich, USA) dissolved in sesame oil at a dosage of 160 mg/kg/day five times a week for a total of two weeks, thereby causing premature ovarian failure. A normal group and the negative control were administered tap water, the positive control was administered 100 mg/kg of metformin, and the group treated only with the *Ulmi* cortex and the experimental group were orally administered the UCE at a concentration of 300 mg/kg simultaneously with VCD for 2 weeks, followed by oral administration for another one week after VCD treatment was completed, wherein a total administration period was three weeks. Thereafter, as described below, uterine and ovarian tissues were visually observed, and an effect of the *Ulmi* cortex extract on protecting the ovaries and uterus was identified through comparison between ovarian weights with respect to body weight.

7-3. Visual Observation of Uterine and Ovarine Tissues

Figure 8:
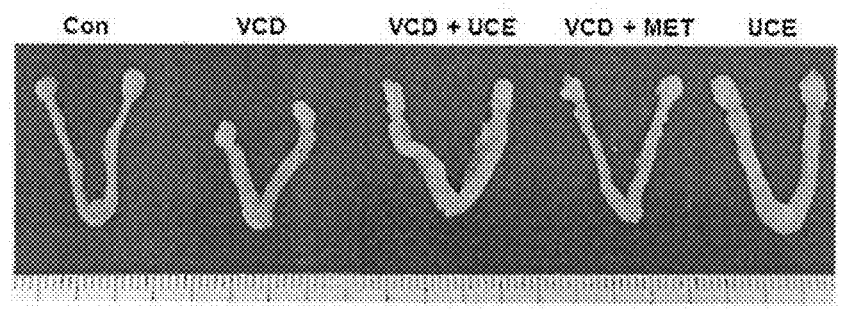
FIG. 8 illustrates visual observation results of uterine and ovarian tissues in a control (Con) and according to treatment with VCD, VCD+*Ulmi* cortex extract (UCE), VCD+metformin (MET), and an *Ulmi* cortex extract (UCE)

FIG. 8 illustrates a visual observation image of the uterine and ovarian tissues. As illustrated in FIG. 8, the sizes of both the ovary and the uterus were maintained normally in the normal group, whereas the sizes of the ovary and the uterus were significantly decreased in the negative control (VCD) and similar sizes of the ovary and the uterus to those of the normal group were maintained in the experimental group (VCD+UCE) and the positive control (VCD+MET). No specific findings were found in the group (UCE) treated only with the UCE.

7-4. Measurement of Body weight and Ovarian Weight

Figure 9:
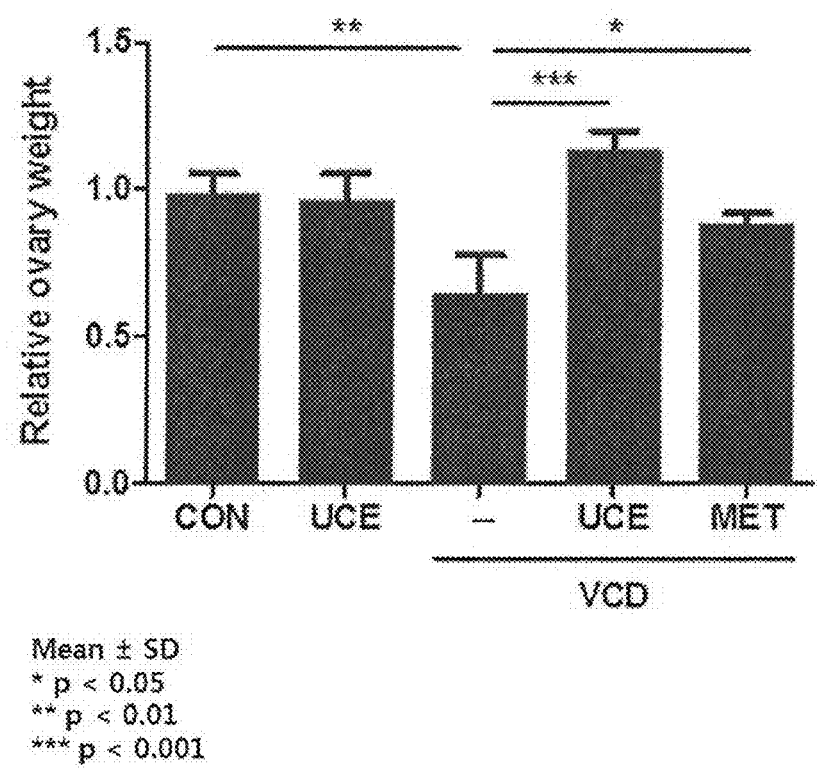
FIG. 9 illustrates an ovary weight index according to treatment with an *Ulmi* cortex extract according to the present disclosure.

Body weight changes were observed every week, based on the body weight measured on the start day of the experiment (day 1). On the last day of the experiment, mice were sacrificed and the uterus and ovaries were removed and tissues were compared with each other according to group. One ovary was removed and the ovarian weight was measured and an ovarian weight index was calculated as a ratio of the measured ovarian weight with respect to the body weight immediately before sacrifice. FIG. 9 illustrates an ovarian weight index calculated as a ratio of ovarian weight to body weight. As illustrated in FIG. 9, a significant decrease compared to the normal group (CON) was seen in the negative control, a significant increase compared to the negative control was seen in the experimental group (VCD+UCE) and an increase compared to the positive control was seen in the experimental group (VCD+UCE), whereas no change in ovarian weight index was seen in the group (UCE) treated only with the UCE. It was confirmed that upon administration of the UCE, the UCE had an effect of inhibiting or preventing a decrease in ovarian weight, caused by VCD.

As is apparent from the foregoing description, an *Ulmi cortex* extract according to the present disclosure can inhibit ovarian aging by inhibiting the oxidative stress or ovotoxicity of the ovaries, and can have an effect of preventing, alleviating, or treating premature ovarian failure or infertility.

The above description of the present disclosure is provided only for illustrative purposes, and it will be understood by one of ordinary skill in the art to which the present disclosure pertains that the invention may be embodied in various modified forms without departing from the spirit or essential characteristics thereof. Thus, the embodiments described herein should be considered in an illustrative sense only and not for the purpose of limitation.

What is claimed is:

1. A method of inhibiting ovotoxicity, the method comprising administering an aqueous or ethanolic extract of *Ulmi macrocarpa* Hance cortex to an individual in need thereof.

2. The method of claim 1, wherein the aqueous or ethanolic extract of *Ulmi macrocarpa* Hance cortex is effective in the treatment of ovarian aging caused by ovotoxicity.

3. The method of claim 2, wherein the ovarian aging comprises one selected from premature ovarian failure and early menopause.

* * * * *